US011249021B2

(12) United States Patent
Pedersen

(10) Patent No.: US 11,249,021 B2
(45) Date of Patent: Feb. 15, 2022

(54) APPARATUS FOR THE INCUBATION OF A BIOLOGICAL MATERIAL

(71) Applicant: ESCO Medical Aps, Egâ (DK)

(72) Inventor: Thomas William Pedersen, Skanderborg (DK)

(73) Assignee: ESCO Medical Aps, Egâ (DK)

( * ) Notice: Subject to any disclaimer, the term of this patent is extended or adjusted under 35 U.S.C. 154(b) by 0 days.

(21) Appl. No.: 16/312,025

(22) PCT Filed: Jun. 30, 2017

(86) PCT No.: PCT/DK2017/050222
§ 371 (c)(1),
(2) Date: Dec. 20, 2018

(87) PCT Pub. No.: WO2018/001437
PCT Pub. Date: Jan. 4, 2018

(65) Prior Publication Data
US 2019/0376012 A1    Dec. 12, 2019

(30) Foreign Application Priority Data

Jun. 30, 2016    (DK) .......................... PA 2016 00390

(51) Int. Cl.
*G01N 21/64*    (2006.01)
*C12M 3/00*    (2006.01)
(Continued)

(52) U.S. Cl.
CPC ......... *G01N 21/6408* (2013.01); *C12M 21/06* (2013.01); *C12M 25/06* (2013.01);
(Continued)

(58) Field of Classification Search
CPC ......... G01N 21/6408; G01N 2021/641; G01N 21/6413; G01N 21/6415; G01N 2021/6413; G01N 2021/6415
See application file for complete search history.

(56) References Cited

U.S. PATENT DOCUMENTS 5,397,709 A * 3/1995 Berndt ................. G01N 21/253
                                                                 356/442
2004/0254474 A1   12/2004 Seibel et al.
(Continued)

FOREIGN PATENT DOCUMENTS

WO         0231477 A2    4/2002
WO      2009003487 A2    1/2009
(Continued)

OTHER PUBLICATIONS

"Fluorescence Lifetime Imaging (FLIM)", Web.archive.org from Apr. 12, 2016 on page www.picoquant.com. Choose Applications and then Lifescience1.
(Continued)

*Primary Examiner* — Chih-Cheng Kao
(74) *Attorney, Agent, or Firm* — Elmore Patent Law Group, P.C.; Joseph C. Zucchero; Carolyn S. Elmore

(57) ABSTRACT

The invention relates to an apparatus (200) for incubation of a viable biological material (2); said apparatus comprises: a housing (4) having an extension in a longitudinal direction X, in a transversal direction Y, and in a direction Z perpendicular to the longitudinal direction and the transversal direction; said housing comprising: two or more culture dish compartments (6), each being adapted to accommodate, one or more culture dishes (8) comprising a biological material (2); wherein said apparatus comprises an image capturing device (10); wherein said apparatus comprises a control unit (12) for controlling the operation thereof; wherein at least part of said image capturing device is being configured to be movable in relation to the two or more culture dish compartments (6), thereby allowing capture of images of one or more of said biological materials (2) accommodated in said one or more culture dishes (8); and wherein said apparatus comprises a FLIM unit (11) (fluorescent lifetime imaging microscope); wherein at least part of said FLIM unit (11) is
(Continued)

being configured to be movable in relation to the two or more culture dish compartments (6), thereby allowing capture of FLIM spectra of one or more of said biological materials (2) accommodated in said one or more culture dishes (8).

23 Claims, 6 Drawing Sheets

(51) Int. Cl.
     *C12M 1/12*           (2006.01)
     *C12M 1/34*           (2006.01)

(52) U.S. Cl.
     CPC .............. *C12M 41/12* (2013.01); *C12M 41/34* (2013.01); *C12M 41/38* (2013.01)

(56) References Cited

U.S. PATENT DOCUMENTS

| | | |
|---|---|---|
| 2005/0181383 A1 | 8/2005 | Su et al. |
| 2009/0021746 A1 | 1/2009 | Toida et al. |
| 2010/0090127 A1* | 4/2010 | Yekta ................. G01N 21/6408 250/459.1 |
| 2011/0137126 A1* | 6/2011 | French ................. A61B 5/0068 600/178 |
| 2013/0126755 A1* | 5/2013 | Kemnitz ............ G01N 21/6456 250/459.1 |
| 2015/0346100 A1* | 12/2015 | Racowsky ......... G01N 21/6408 435/34 |

FOREIGN PATENT DOCUMENTS

| | | |
|---|---|---|
| WO | 2011/025736 A1 | 3/2011 |
| WO | 2014/110008 A1 | 7/2014 |
| WO | 2014/131091 A1 | 9/2014 |
| WO | 2015/001396 A1 | 1/2015 |
| WO | WO-2015001396 A1 * | 1/2015 ............ C12M 41/46 |

OTHER PUBLICATIONS

"GI85 IVF Tri-Gas Incubator", Labivf Asia PTE LTD: Internet Citation, [Online], Jan. 31, 2010 (Jan. 31, 2010), pp. 1-4, XP002722520, Retrieved from the Internet:URL:http://www.labivf.com/index.cfm?GPID=23> [retrieved on Mar. 31, 2014].

Sun, Y., "Localizing protein-protein interactions in living cells using fluorescence lifetime imaging microscopy", Methods in molecular biology, vol. 1251, 2015, 83-107.

\* cited by examiner

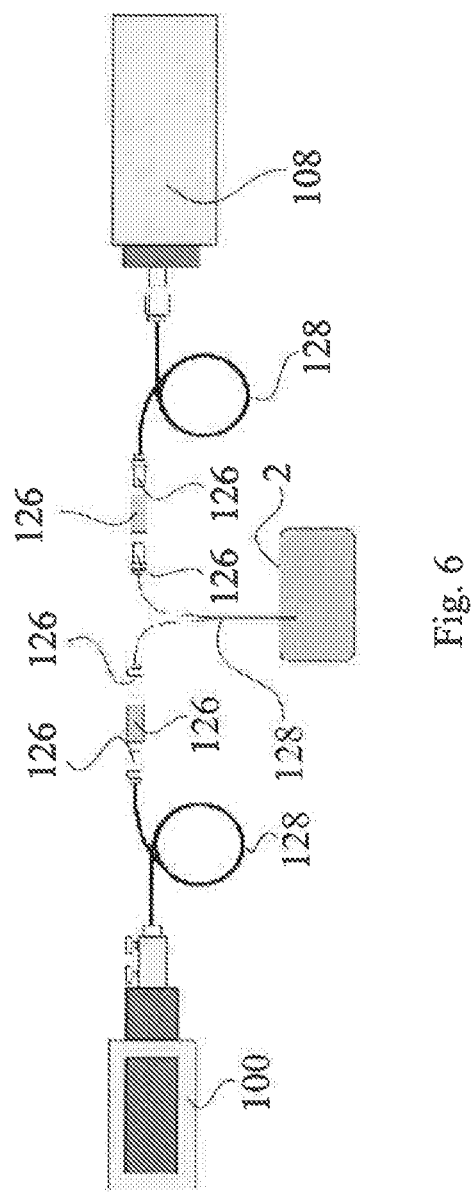

APPARATUS FOR THE INCUBATION OF A BIOLOGICAL MATERIAL

FIELD OF THE INVENTION

The present invention relates to the field of in vitro fertilization. More specifically the present invention relates in a first aspect to an apparatus for incubation of a biological material. In a second aspect the present invention related to a system for incubation of a biological material. In a third aspect the present invention relates to a use of an apparatus according to the first aspect or of a system according to the second aspect for incubation of a biological material. In a fourth aspect the present invention relates to a method for assessing optimum incubation conditions for a viable biological material. In a fifth aspect the present invention relates to a method for selecting a specific biological material having the highest quality, amongst an array of biological materials.

BACKGROUND OF THE INVENTION

The development of in vitro fertilization (IVF) has for the last few decades resulted in considerably improved methods and techniques thus leading to improved success rates in terms of enhanced rates of successful births originating from such techniques.

In vitro fertilization involves capturing a ripened egg from a female ovary, fertilizing the ovary with a spermatozoon, incubating the fertilized egg under a controlled environment and subsequently inserting the fertilized and incubated egg in a female's uterus.

As in vitro fertilization is most commonly used by females or couples which notoriously are having problems in getting pregnant the natural way, thus implying some degree of reduced fertility by the male or female counterpart of the couple, or both, and as in vitro fertilization techniques involves quite expensive procedures, these in vitro fertilization techniques are usually performed in a way that seek to optimize efficiency, especially in view of the fact that frequently more than one insertion of a fertilized egg into the female' uterus will be necessary in order to encounter a successful pregnancy.

Accordingly, in order to make the in vitro fertilization techniques efficient, the female is typically provided with a hormone treatment prior to harvesting eggs from her ovary.

Such hormone treatment will make the female ovary ovulate not only one egg, but a multitude of eggs at the same time.

In order to increase the chance of a viable and successful pregnancy more than one egg from the same female will accordingly be fertilized and incubated concurrently in an incubator.

Prior art incubators include a compartment which may be controlled in respect of temperature, moisture and composition of atmosphere. Most incubator's compartment allows for accommodating more than one culture dish comprising the fertilized eggs.

However, it is not an easy task to perform a successful in vitro fertilization and incubation of an egg.

One of the major reasons for the rather low success rate of in vitro fertilizations is the absence of reliable methods for selecting the highest quality embryo(s) for transfer.

The lack of methods for assessing embryo quality has led to substantial efforts to develop improved assays of embryo viability. The current most reliable method for predicting embryo quality is to examine embryo morphology prior to transfer using standard transmitted light microscopy systems.

In methods for examination of embryo morphology quality, camera means are providing within the prior art incubators and these may be equipped with a microscopic optics which allow for capturing close-up images of each fertilized egg with the view to only select those eggs that exhibit a normal or healthy development and to only insert those eggs in to the female's uterus.

In recent years it has been common practice to equip the camera means with time lapse image processing means for better allowing selection of the right fertilized eggs for subsequent insertion into the uterus.

Time lapse imaging provides for visual study of the visible physical development, such as time of division of cells at different stages, overall speed of division of cells. Studies of spindle may represent another mode of assessing the stage of development of such in an embryo.

However, selection criteria generally remain subjective and only result in a ~35% success rate.

Newly proposed non-microscopy based methods, using genomic, transcriptomic or proteomic based assays, require a biopsy of the embryo and are thus invasive and significantly reduce rates of embryo survival. A metabolomic approach which initially showed promise was to assay the metabolic state of the embryo by measuring changes in metabolites in the embryo culture media. However, a prospective randomized trial has recently failed to show that utilization of such metabolomic assessment improves selection over morphologic evaluation alone.

For improving the safety of the mother and the fetus, and also for reducing the costs of the assisted reproductive technologies by reducing the number of times one has to try implantation to get pregnant and also by reducing multiple gestations, it is preferred to employ minimally invasive, simple and reliable methods for assessing embryo or oocyte viability.

Although time lapse image capturing using image capturing in the visible spectrum may have proven useful for certain applications within the field of monitoring development of biological samples in in vitro fertilization techniques, such image capturing device suffer from important drawbacks.

Such drawbacks resides in the fact that using a time lapse image capturing device working in the visible spectrum only the part of the biological material which is closest to the objective of the optics of the image capturing device will in fact be visible and hence captured by the image capturing device.

In other words, biological material which is closest to the objective of the optics of the image capturing device will shadow for the optics in such a way that lower lying material of the biological sample may not be visible and hence may not provide important and interesting information relating to the development of the biological material.

The result is that in using a time lapse image capturing device working in the visible spectrum when monitoring the development of a biological sample, important physical changes in the biological sample taking place in areas which is not in immediate vicinity of the objective of the optics of the image capturing device may not be detected and hence the information retrieved using light in the visible spectrum in a time lapse image capturing device for monitoring a biological sample may be quite limited.

In recent years an alternative microscopic technique has been developed. This technique is denoted fluorescent lifetime imaging microscopy (FLIM).

In fluorescent lifetime imaging microscopy fluorophores of the biological material are brought into an exited state by subjecting the biological sample to a very short pulse of electromagnetic radiation. Subsequently, within a certain delay time, the fluorophore returns to its energetic ground state with the result of emitting electromagnetic radiation.

The time span between the short pulse of electromagnetic radiation on the one hand and the emission of electromagnetic radiation from the fluorophore on the other hand will be indicative of the metabolic state of the viable biological material in that on number of naturally occurring substances involved in the metabolism of the biological material are fluorophores. Examples of such fluorophores are nicotine amide adenine (NADH) and flavine adenine dinucleotide (FAD).

Accordingly, in Fluorescence Lifetime Imaging an image is produced based on the differences in the excited state decay rate from a fluorescent sample. Thus, FLIM is a fluorescence imaging technique where the contrast is based on the lifetime of individual fluorophores rather than their emission spectra. The fluorescence lifetime is defined as the average time that a molecule remains in an excited state prior to returning to the ground state by emitting a photon.

Time-Correlated Single Photon Counting (TCSPC) is used to determine the fluorescence lifetime. In TCSPC, one measures the time between sample excitation by a pulsed laser and the arrival of the emitted photon at the detector. TCSPC requires a defined "start", provided by the electronics steering the laser pulse or a photodiode, and a defined "stop" signal, realized by detection with single-photon sensitive detectors (e.g. Single Photon Avalanche Diodes, SPADs). The measurement of this time delay is repeated many times to account for the statistical nature of the fluorophores emission. The delay times are sorted into a histogram that plots the occurrence of emission over time after the excitation pulse. In order to acquire a fluorescence lifetime image, the photons have to be attributed to the different pixels, which is done by storing the absolute arrival times of the photons additionally to the relative arrival time in respect to the laser pulse. Line and frame marker signals from the scanner of the confocal microscope are additionally recorded in order to sort the time stream of photons into the different pixels.

Cells with objectively measured adequate metabolic state as indicated by fluorescent lifetime of protein bound and/or free NAHD or protein bound and/or free FAD indicate an oocyte or embryo that can be selected for in vitro fertilization or implantation, and if the metabolic state is inadequate the oocyte/embryo can be discarded from in vitro fertilization or implantation.

Accordingly, by registering the delay in emission of electromagnetic radiation from the fluorophores, relative to the time of imparting a pulse of radiation to which the fluorophore has been subjected, a map of the biological material can be obtained, whereby even areas which are not located in or at the surface of the biological material may studied.

Such mapping can be used to compare the metabolic state of one biological material with the metabolic state of another biological material. However, when performing such comparison, it is important in respect of obtaining reliable results that the biological materials being compared are at comparable development stages. That is, in order to provide a comparative analysis by means of FLIM spectra in respect of e.g. two different viable biological materials one needs to ensure that the two viable biological materials are at a comparative stage of development—otherwise the metabolic stages, as expressed by the FLIM spectra, of the biological materials cannot really be compared.

The present invention aims at providing apparatuses, uses and methods for allowing improving studies of development of biological samples under strictly controlled environmental conditions, such as in relation to temperature and composition of the surrounding atmosphere.

Especially, the present invention aims at providing apparatuses, uses and methods for determination of optimum incubation conditions for viable biological materials in the form of embryos or oocytes which are to be inserted into the uterus of a human female.

BRIEF DESCRIPTION OF THE INVENTION

This objective is fulfilled with the present invention in its various aspects. Accordingly, the present invention relates in a first aspect to an apparatus for incubation of a viable biological material;

said apparatus comprises:

a housing having an extension in a longitudinal direction, in a transversal direction, and in a direction perpendicular to the longitudinal direction and the transversal direction; said housing comprising:

two or more culture dish compartments, each being adapted to accommodate, one or more culture dishes comprising a biological material;

wherein said apparatus comprises an image capturing device;

wherein said apparatus comprises a control unit for controlling the operation thereof;

wherein at least part of said image capturing device is being configured to be movable in relation to the two or more culture dish compartments, thereby allowing capture of images of one or more of said biological materials accommodated in said one or more culture dishes; and wherein said apparatus comprises a FLIM unit (fluorescent lifetime imaging microscope)

wherein at least part of said FLIM unit is being configured to be movable in relation to the two or more culture dish compartments, thereby allowing capture of FLIM spectra of one or more of said biological materials accommodated in said one or more culture dishes.

In its second aspect the present invention relates to a system for incubation of a viable biological material;

said system comprises:

an apparatus according to the first aspect of the present invention in combination with one or more culture dishes.

In its third aspect the present invention relates to a use of an apparatus according to the first aspect of the present invention or of a system according to the second aspect of the present invention for incubation of a viable biological material.

In its fourth aspect the present invention relates to a method for assessing optimum incubation conditions for a viable biological material, said method comprising the following steps:

i) providing an apparatus according to the first aspect of the present invention or providing a system according to the first aspect of the present invention;

ii) accommodating at least two culture dishes, each comprising one or more viable biological materials in separate culture dish compartments of said apparatus;

iii) incubating said biological materials at incubation conditions, wherein the physical and/or chemical incubation conditions in respect of biological material being accommodated in one culture dish compartment differs by one or more parameters from the physical and/or chemical incubation conditions in respect of biological material being accommodated in another culture dish compartment;

iv) during step iii), using the FLIM unit of said apparatus for capturing FLIM spectra;

v) assessment of the quality of the biological material based on said FLIM spectra.

In a fifth aspect the present invention relates to a method for selecting a specific biological material having the highest quality, amongst an array of biological materials, wherein said method comprises:

a) providing an apparatus according the first aspect of the present invention;

b) incubating said array of biological materials in said apparatus;

c) in respect of each specific of said array of biological materials, use said image capturing device to identify a predetermined morphological state of said specific biological material;

d) in the event that a predetermined morphological state has been reached in respect of a specific biological material, use said FLIM unit to capture a FLIM spectrum of said specific biological material;

e) comparing the FLIM spectra obtained in respect of said array of biological materials and associated with the same morphological state of that material;

f) based on the comparison made in step e), selecting that specific biological material having the highest quality, based on one or more predetermined criteria.

The present invention in its various aspects provides for improved monitoring development of a biological material, such as a viable biological material because the FLIM unit allows for looking deeper into the tissue of the biological material.

This is especially important for research purposes in which a vast array of different incubation environments and/or incubation conditions and/or incubation protocols are tried out in order to—by trial and error—to find the most optimum incubation environments and/or incubation conditions and/or incubation protocols for the biological material. In a specific embodiment such optimizations relate to finding optimum incubation environments and/or incubation conditions and/or incubation protocols for an oozyte or an embryo.

With the apparatus, the system, the use and the method according to the present invention it is possible to conduct a number of almost identical incubations of biological materials, wherein only one parameter relating to physical and/or chemical incubation conditions differs between conditions in respect of two biological materials.

Thereby the effect of varying only one parameter relating to physical and/or chemical incubation conditions may be determined. This in turn may be utilized for determining the collective optimum parameters relating to physical and/or chemical incubation conditions.

Such optimization is possible because the apparatus of the present invention comprises two or more culture dish compartments, each being adapted to accommodate, one or more culture dishes comprising a biological material.

For almost all fluorophores, the rate of energy transfer to the environment depends on the concentration of ions, oxygen, pH value or the binding of proteins in a cell. There is a direct relation between the concentrations of these ions, called fluorescence quenchers, and the fluorescence lifetime of the fluorophore.

Hence, FLIM can not only be used to discriminate between different fluorophores on the basis of their characteristic lifetimes (rather than their spectral properties) but also to distinguish among different environments within the cell based on changes in lifetime of the same fluorophore if it is present in local environments containing varying concentrations of fluorescence quenchers.

This means that metabolism of a viable biological material may be studied with the present invention based on effects of various fluorophore environments, such as polarity, pH, temperature, ion concentration etc.

Also, using the present invention detection of molecular interactions allowing for distance measurements in the nanometer range will be possible. Again, this may be done with reference to various incubation conditions.

Yet another concept which may be studied using the present invention is a detection of conformational intramolecular changes due to folding or action of molecular motors.

A still further concept which may be studied using the present invention is the ability to distinguish employed fluorophores and determine their spectral characteristics, as well as discriminating label fluorescence from the fluorescence background of the a viable biological material, thus allowing an improved detection efficiency and more accurate marker localization.

Yet a still further concept which may be studied using the present invention is characterization and quality control of new materials via fluorescent labels or quantum dots.

Using the apparatus of the invention in the studies provides for constructing a database comprising data retrieved form the FLIM microscopy of the viable biological material. By comparing the actual viability of various different biological materials and by comparing these material's FLIM spectra makes it possible to predict those pointers or features in a FLIM spectrum that correspond to a "healthy" viable biological material.

Hence, based on statistical analysis it will be possible, using the apparatus according to the present invention, to assess the quality of a specific viable biological material, such as an oocyte or an embryo.

BRIEF DESCRIPTION OF THE FIGURES

FIG. 6 illustrates one embodiment laser diode/detector set-up using optical cables.

DETAILED DESCRIPTION OF THE INVENTION

Figure 1:
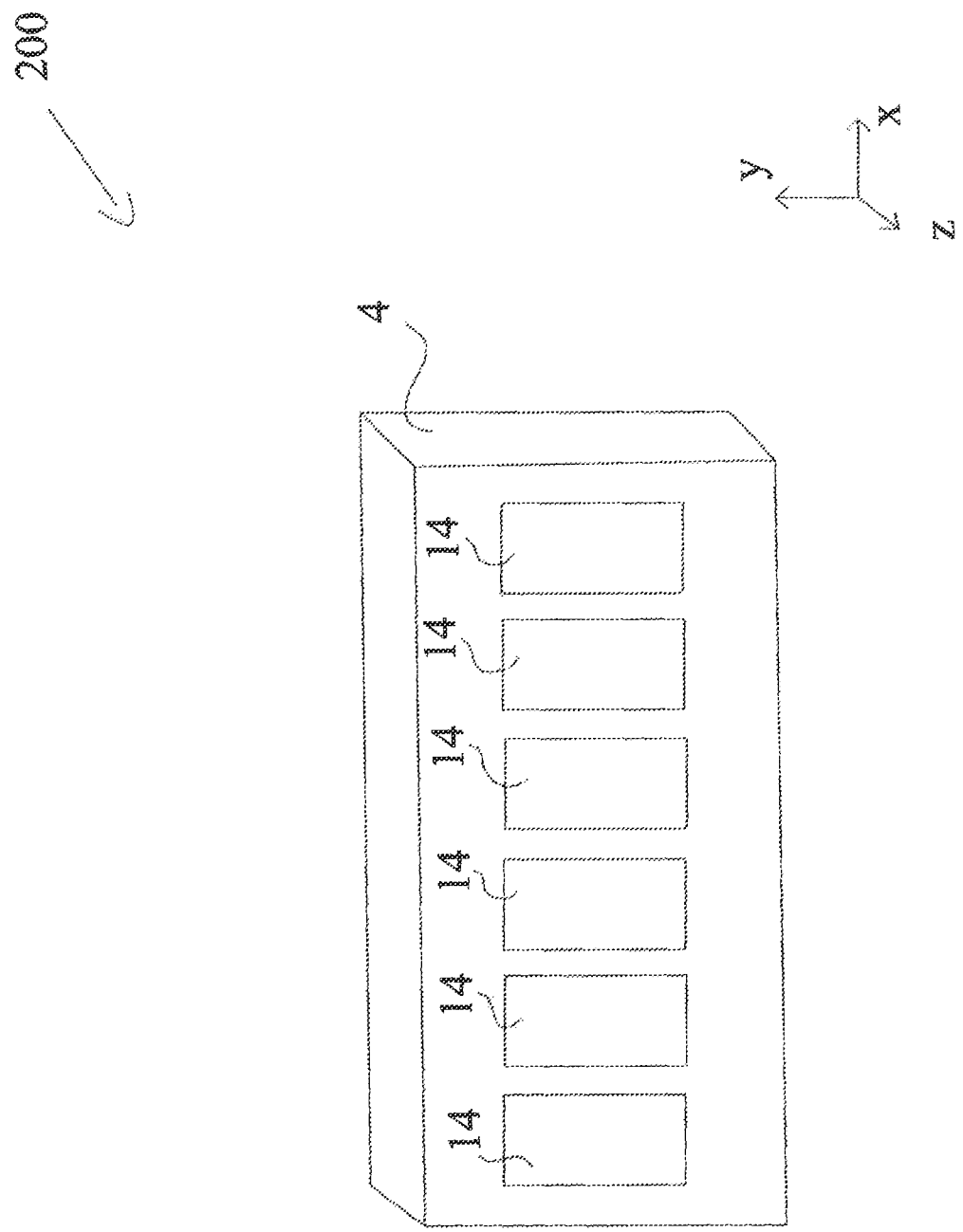
FIG. 1 shows in a perspective view an embodiment of a device according to the present invention.

The present invention relates in a first aspect to an apparatus for incubation of a viable biological material; said apparatus comprises:

a housing having an extension in a longitudinal direction, in a transversal direction, and in a direction perpendicular to the longitudinal direction and the transversal direction; said housing comprising:

two or more culture dish compartments, each being adapted to accommodate, one or more culture dishes comprising a biological material;

wherein said apparatus comprises an image capturing device;

wherein said apparatus comprises control unit for controlling the operation thereof;

wherein at least part of said image capturing device is being configured to be movable in relation to the two or more culture dish compartments, thereby allowing capture of images of one or more of said biological materials accommodated in said one or more culture dishes; and wherein said apparatus comprises a FLIM unit (fluorescent lifetime imaging microscope)

wherein at least part of said FLIM unit is being configured to be movable in relation to the two or more culture dish compartments, thereby allowing capture of FLIM spectra of one or more of said biological materials accommodated in said one or more culture dishes.

Accordingly, the apparatus of the first aspect of the present invention is an apparatus for incubation of a viable biological material and it comprises an image capturing device as well as a FLIM unit.

Hereby it is achieved that during incubation of a biological material, such as an oocyte or an embryo, the morphological state of the biological material can be monitored by means of the image capturing device, whereas the metabolic state of the biological material can be monitored by using the FLIM unit. This is possible in part because the image capturing device and the FLIM unit, or at least parts thereof, are movable in relation to the culture dish compartments. The image capturing device and the FLIM unit may be movable individually or collective on a set of common movement means.

Collectively, this provides for an improved basis for determining the quality of a biological material, especially in case of an oocyte or an embryo, with the view to select that species which has the highest prospect of leading to a successful pregnancy when inserted into a female's uterus.

In one embodiment of the first aspect of the present invention the number of individual culture dish compartments is being 2-25, for example 3-24, such as 4-23, e.g. 5-22, such as 6-21, e.g. 7-20 or 8-19, for example 9-18, such as 10-17, for example 11-16, such as 12-15 or 13-14 individual culture dish compartments.

Such numbers of individual and/or separate culture dish compartments allows in a research situation to conduct a number of parallel protocols wherein each protocol differs by only one parameter from one culture dish compartment to another. Thereby optimization of protocols of a specific type of viable biological material may be determined.

In one embodiment of the first aspect of the present invention one or more of said individual culture dish compartments, preferable all said culture dish compartments comprises its own individual lid, wherein each said lid is configured to be able to shift between an open configuration providing access to the corresponding culture dish compartment and a closed configuration in which the corresponding culture dish compartment is being sealed off from the surroundings.

By providing individual and separate culture dish compartments with its own individual lid, it is assured that the environment of one culture dish compartment may be kept at predetermined conditions independent of the environment of the other culture dish compartments.

In one embodiment of the first aspect of the present invention the apparatus furthermore comprising temperature regulating means for individual and independent regulation of the temperature in one or more of said individual culture dish compartments, preferable in each of said individual culture dish compartments.

By providing individual and separate culture dish compartments with its own individual temperature regulating means for individual regulating the temperature, it is assured that the environment of one culture dish compartment may be kept at predetermined conditions independent of the environment of the other culture dish compartments.

In one embodiment of the first aspect of the present invention said temperature regulating means independently comprising heating means, such as one or more electric heating elements; and/or cooling means, such as one or more Peltier elements.

In one embodiment of the first aspect of the present invention the apparatus furthermore comprising gas composition regulating means for individual regulating the gas composition, such as the concentration of oxygen, carbon dioxide and/or nitrogen in one or more of said individual culture dish compartments, preferable in each of said individual said culture dish compartments.

In one embodiment of the first aspect of the present invention said apparatus comprising means for supplying one or more types of different gases from an external source, such as from a gas cylinder.

In one embodiment of the first aspect of the present invention said means being valves for regulating the flow of gas into the apparatus.

In one embodiment of the first aspect of the present invention said apparatus comprising a gas mixing box for said one or more gases.

By providing individual and separate culture dish compartments with its own individual gas composition regulating means for individual regulating the gas composition, it is assured that the environment of one culture dish compartment may be kept at predetermined conditions independent of the environment of the other culture dish compartments.

In one embodiment of the first aspect of the present invention said gas mixing box comprises a $CO_2$ sensor, such as a NDIR $CO_2$ sensor; and a $O_2$ sensor, such as a medical grade chemical $O_2$ sensor, and furthermore comprises one or more conduits for conducting a gas from said gas mixing box to one or more of said separate culture dish compartments.

Such sensors allows for monitoring the environment to be supplied to the particular culture dish compartment(s).

In one embodiment of the first aspect of the present invention said two or more culture dish compartments share the same gas mixing box; or alternatively each culture dish compartment is assigned its own individual gas mixing box.

In one embodiment of the first aspect of the present invention the apparatus comprises means for subjecting said one or more gas or mixture of gases to UV radiation, such as UV-C radiation, said means optionally comprises a filter for filtering off UV radiation which could lead to the production of ozone, such as UV radiation having a wavelength of 175-195 nm, such as UV radiation having a wavelength of 180-190 nm.

In one embodiment of the first aspect of the present invention the apparatus furthermore comprising means for filtering the gas or mixture of gases, such as HEPA filter and/or a carbon filter prior to entering the culture dish compartment.

Such UV radiation means and/or filter means provide for sanitizing the gas to be supplied to the culture dish compartment(s).

In one embodiment of the first aspect of the present invention said apparatus in respect of one or more of said culture dish compartments comprise one or more conduits for leading gas from said culture dish compartment to a gas mixing box.

In one embodiment of the first aspect of the present invention said individual culture dish compartment in respect of one or more of said individual culture dish compartments, preferably in respect of each individual culture dish compartment, comprises a transparent shelf for carrying a culture dish; and wherein said image capturing device and said FLIM unit, or at least the parts thereof transmitting and receiving electromagnetic radiation, is/are arranged below said shelves and being adapted to be movable so as to enable transmitting and/or capturing electromagnetic radiation, through said shelves, to/from said biological material accommodated in any of said culture dish being accommodated in any of said culture dish compartments.

Hereby is achieved that the FLIM unit or at least a light transmitting and a light receiving part of it may be arranged below the culture dish(es) whereby one FLIM unit may be able to capture images associated with culture dishes being accommodated in different culture dish compartments.

In one embodiment of the first aspect of the present invention the individual culture dish compartment, in respect of one or more of said individual culture dish compartments, preferably in respect of each individual culture dish compartment, independently comprises one or more of the following: a pH sensor, a temperature sensor, an oxygen sensor, a carbon dioxide sensor.

Such sensors allows for monitoring the environment in the particular culture dish compartment.

In one embodiment of the first aspect of the present invention said control unit for controlling the operation of said apparatus is configured to independently control one or more of the following: said temperature regulating means in respect of one or more of the culture dish compartments; said gas composition regulating means in respect of one or more of the culture dish compartments; said image capturing device; or said FLIM unit.

In one embodiment of the first aspect of the present invention said control unit being configured to allow a user to input predetermined operation protocol(s) to be followed by said apparatus; and wherein said control unit being configured to control said apparatus according to said protocol(s).

Hereby is achieved that the apparatus may be operated fully automatically according to predetermined protocols.

In one embodiment of the first aspect of the present invention said apparatus comprises input means, su as an alphanumerical keyboard, for allowing a user to program and select one or more operation protocols to be followed by said apparatus; and/or for allowing a user to program specific protocols to be followed by said apparatus.

In one embodiment of the first aspect of the present invention said apparatus comprises a display for displaying to an operator details relation to status and progression of the operation of the apparatus.

Such display means allows an operator to control and monitor the operation of the apparatus.

In one embodiment of the first aspect of the present invention said apparatus further comprising an image processing unit for processing images captured by said image capturing device; and/or further comprising a spectral data processing unit for processing information relating to electromagnetic radiation captured by said FLIM unit.

In one embodiment of the first aspect of the present invention said image processing unit being configured to provide, from the images captured by said image capturing device, time-lapse image series of one or more specific biological materials of the biological materials being incubated.

Time lapse imaging allows one to monitor the development of a particular viable biological material with the view to assess the quality of such a material with the view to selecting a particular biological material for further processing steps.

In one embodiment of the first aspect of the present invention said spectral data processing unit is being configured to be able to perform an analysis of differences between two identified spectra captured by said FLIM unit.

Hereby is achieved that an objective assessment of the quality of a metabolic state of a biological material can be obtained.

In one embodiment of the first aspect of the present invention said FLIM unit independently comprises one or more of the following elements:
  a laser source, such as a pulsed laser source, such as a diode laser or a multiphoton excitation laser;
  a single photon sensitive detector;
  a dichroic mirror (for separation of fluorescence signal from the excitation light);
  an objective (for focusing excitation light into sample and/or for collecting fluorescence signal);
  a control system for controlling said FLIM unit.

In one embodiment of the first aspect of the present invention said laser source being coupled to optical means for conveying electromagnetic radiation, such as one or more optical fibers, said optical means comprising a distal end being configured to be directed close to the biological material, for conveying by transmission, electromagnetic radiation.

Hereby is achieved that the part of the FLIM unit responsible for transmitting and receiving electromagnetic radiation may easily be moved relative to the biological material being under investigation.

In one embodiment of the first aspect of the present invention said single photon sensitive detector independently being coupled to optical means for conveying electromagnetic radiation, such as one or more optical fibers, said optical means comprising a distal end being configured to be directed to the biological material, for conveying by receiving, electromagnetic radiation.

In one embodiment of the first aspect of the present invention said FLIM unit is configured for auto-fluorescence of nicotine amide adenine (NADH) and/or for auto-fluorescence of flavine adenine dinucleotide (FAD) being involved in the metabolism of the biological material.

In one embodiment of the first aspect of the present invention said apparatus being configured for operating in a time-correlated single photon counting (TCSPC) mode.

In one embodiment of the first aspect of the present invention said apparatus being configured for operating in a FRET mode or in a FRAP mode or in a PLIM mode (Phosphorescence Lifetime Imaging Microscopy).

In one embodiment of the first aspect of the present invention said laser is operating in the wavelength range of 350-800 nm, such as 400-750 nm, for example 450-700 nm, e.g. 500-650 nm, such as 550-600 nm.

In one embodiment of the first aspect of the present invention said laser is operating in pulse widths of 30-100, such as 40-90, e.g. 50-80, such as 60-70 picoseconds (ps).

In one embodiment of the first aspect of the present invention said apparatus during the fluorescence operations is being configured to operate in the time domain or in the frequency domain.

Such modes of operation and ranges of parameters have proven beneficial for the intended study of the biological material.

In one embodiment of the first aspect of the present invention said apparatus is being configured to incubate two or more biological material in the form of oocytes or embryos; wherein said apparatus in respect of each specific of said two or more biological materials is being configured, based on images captured by said image capturing device, to identify a predetermined morphological state of said specific biological material; and wherein said apparatus is being configured, in the event that a predetermined morphological state has been reached in respect of a specific biological material, to capture a FLIM spectrum of said specific biological material.

Hereby is achieved that the metabolic state and quality of two or more oocytes or embryos can be compared at the same morphological state.

In one embodiment of this embodiment said apparatus is being configured, in respect of each specific of said two or more biological materials, to identify two or more different and predetermined morphological states, based on said images captured by said image capturing device, of that specific biological material, and wherein in the event of each such different and predetermined morphological state has been reached in respect of a specific biological material, said apparatus is being configured to capture a FLIM spectrum of said specific biological material in respect of each such predetermined morphological state.

Hereby is achieved that the development or change in metabolic state and quality of two or more oocytes or embryos can be compared in the transition from one to another morphological state.

In one embodiment of this embodiment said apparatus in respect of each of said two or more biological materials is being configured for analyzing differences of the FLIM spectra corresponding to two or more different morphological states of the same biological material.

Such analysis may be performed automatically by said apparatus or it may be performed manually in the sense that the apparatus is instructed to perform such an analysis.

In one embodiment of this embodiment said apparatus is being configured to identify that specific biological material exhibiting the smallest difference in FLIM spectra belonging to two different and specific morphological states, as the most stable biological material; and accordingly the best candidate for insertion into a female's uterus.

It has been discovered that those oocytes or embryos which exhibit the smallest change, in terms of the appearance of a FLIM spectrum, when transiting from one morphological state to the next, are prone to lead to the most successful pregnancies when being inserted into a female's uterus.

In one embodiment of these embodiments said morphological state/states is/are selected from the group comprising events associated with the following: t0 (time of insemination), tPB2 (time from insemination to appearance of second polar body); tPNa (time from insemination to pronuclei appearance); tPNf (time from insemination to pronuclei fading); t2-t9 (time from insemination to corresponding divisions (2 to 9)); tM (time from insemination to compacting into morula stage); t5B (time from insemination to start of blastulation); tB (time from insemination to blastocyst formation complete); tEB (time from insemination to expanded blastocyst); tHB (time from insemination to hatched blastocyst); cc1 (first round of cleavage); cc2 (second round of cleavage); cc3 (third round of cleavage); cc4 (fourth round of cleavage); s1 (first synchronization parameter); s2 (second synchronization parameter); s3 (third synchronization parameter); t2_int (stage after first division); t4_int (stage after second division); t8_int (stage after third division).

These events are events that are easily recognizable by an image capturing device and which represent well defined transitions in the development of an oocyte or an embryo. In its second aspect the present invention relates to a system for incubation of a viable biological material;

said system comprises:
an apparatus according to the first aspect of the present invention in combination with
one or more culture dishes.

In one embodiment of the second aspect of the present invention said one or more culture dishes comprises a material comprising a number of culture wells.

In one embodiment of the second aspect of the present invention said number of culture wells being 2-21, such as 3-20, for example 4-19, such as 5-18, for example 6-17, such as 7-16, e.g. 8-15, for example 9-14, such as 10-13 or 11-12.

Such numbers of culture wells allows in a research situation to conduct a number of parallel protocols wherein each protocol differs by only one parameter from one culture well to another. Thereby optimization of protocols for the incubation of a specific type of viable biological material may be determined.

In its third aspect the present invention relates to a use of an apparatus according to the first aspect of the present invention or of a system according to the second aspect of the present invention for incubation of a viable biological material.

In one embodiment of the third aspect of the present invention the biological material is being an oocyte or an embryo.

In one embodiment of the third aspect of the present invention the use is for assessment of the quality of a metabolic state of said viable biological material.

In one embodiment of the third aspect of the present invention the use is for empirically determining optimum protocols relating to physical and/or chemical conditions of a biological material during the incubation thereof.

In its fourth aspect the present invention relates to a method for assessing optimum incubation conditions for a viable biological material, said method comprising the following steps:

i) providing an apparatus according to the first aspect of the present invention or providing a system according to the first aspect of the present invention;

ii) accommodating at least two culture dishes, each comprising one or more viable biological materials in separate culture dish compartments of said apparatus;

iii) incubating said biological materials at incubation conditions, wherein the physical and/or chemical incubation conditions in respect of biological material being accommodated in one culture dish compartment differs by one or more parameters from the physical and/or chemical incubation conditions in respect of biological material being accommodated in another culture dish compartment;

iv) during step iii), using the FLIM unit of said apparatus for capturing FLIM spectra;

v) assessment of the quality of the biological material based on said FLIM spectra In one embodiment of the fourth aspect, the FLIM spectra being captured in step iv) is being captured at predetermined and similar morphological stage(s) in respect of each said biological material.

Hereby it is possible to compare the metabolic state of different biological materials having reached the same morphological stage.

In one embodiment of this embodiment said predetermined and similar morphological stage(s) is/are being determined from images captured by said image capturing device.

In one embodiment of the fourth aspect of the present invention step ii)-v) are repeated, wherein at least one set of physical and/or chemical incubation conditions in respect of biological material being accommodated in one culture dish is being altered.

In one embodiment of the fourth aspect of the present invention the most optimum physical and/or chemical incubation conditions is being determined, based on said FLIM spectra. In a fifth aspect the present invention relates to a method for selecting a specific biological material having the highest quality, amongst an array of biological materials, wherein said method comprises:

a) providing an apparatus according to the first aspect of the present invention;

b) incubating said array of biological materials in said apparatus;

c) in respect of each specific of said array of biological materials, use said image capturing device to identify a predetermined morphological state of said specific biological material;

d) in the event that a predetermined morphological state has been reached in respect of a specific biological material, use said FLIM unit to capture a FLIM spectrum of said specific biological material;

e) comparing the FLIM spectra obtained in respect of said array of biological materials and associated with the same morphological state of that material;

f) based on the comparison made in step e) selecting that specific biological material having the highest quality, based on one or more predetermined criteria.

Hereby is achieved that the metabolic state and quality of two or more biological materials, such as oocytes or embryos can be compared at the same morphological state, and on the basis of the appearance of the FLIM spectra, the biological material having the highest quality can be selected.

In one embodiment of the fifth aspect of the present invention said image capturing device is used in step c) to identify two or more different and predetermined morphological states; and wherein in step d), and in respect of each specific biological material, said FLIM unit is used to capture a FLIM spectrum of said specific biological material at each of the two or more different and predetermined morphological states.

Hereby is achieved that the development or change in metabolic state and quality of two or more oocytes or embryos can be compared in the transition from one to another morphological state.

In one embodiment of the fifth aspect of the present invention, and in respect of each of said biological materials of said array of biological materials, differences of the FLIM spectra corresponding to two different morphological states of the same biological material is analyzed.

In respect of different biological materials, analyzing the FLIM spectra corresponding to two different morphological states of that specific biological material allows one to assess the stability of the metabolism of one biological material compared to the stability of the metabolism of another biological material.

In one embodiment of the fifth aspect of the present invention said method further comprises the step of identifying that specific biological material exhibiting the smallest difference in FLIM spectra belonging to two different and specific morphological states, as the most stable biological material; and accordingly the best candidate for insertion into a female's uterus.

In one embodiment of the fifth aspect of the present invention one or more of said predetermined morphological states are selected from the group comprising events associated with the following: t0 (time of insemination), tPB2 (time from insemination to appearance of second polar body); tPNa (time from insemination to pronuclei appearance); tPNf (time from insemination to pronuclei fading); t2-t9 (time from insemination to corresponding divisions (2 to 9)); tM (time from insemination to compacting into morula stage); t5B (time from insemination to start of blastulation); tB (time from insemination to blastocyst formation complete); tEB (time from insemination to expanded blastocyst); tHB (time from insemination to hatched blastocyst); cc1 (first round of cleavage); cc2 (second round of cleavage); cc3 (third round of cleavage); cc4 (fourth round of cleavage); s1 (first synchronization parameter); s2 (second synchronization parameter); s3 (third synchronization parameter); t2_int (stage after first division); t4_int (stage after second division); t8_int (stage after third division).

These events are events that are easily recognizable by an image capturing device and which represent well defined transitions in the development of an oocyte or an embryo. Referring now to the drawings for the purpose of illustrating preferred embodiments of the present invention, FIG. 1 shows in a perspective view an embodiment of a device 200 according to the first aspect of the present invention. FIG. 1 shows the housing 2 of the device 200. In the embodiment shown in FIG. 1 the device comprises six separate culture dish compartments 6, each having its own lid 14. The housing extends in a longitudinally direction X and in a transverse direction Y and in a direction Z perpendicular to the longitudinal direction and the transversal direction. The six separate culture dish compartments 6 are aligned along the X direction.

Figure 2:
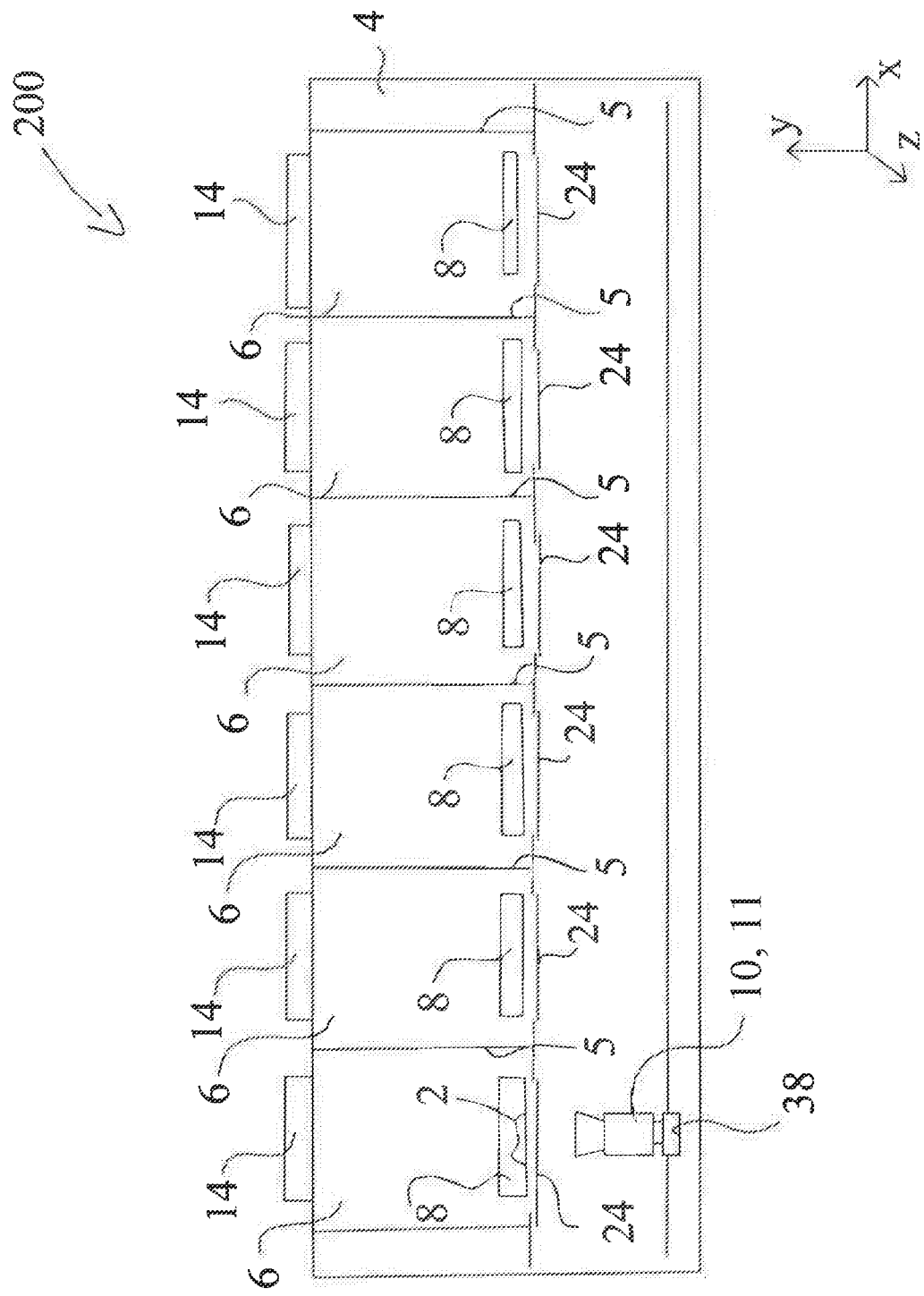
FIG. 2 shows schematically the principle of the device according to the present invention.

FIG. 2 shows schematically a device 200 according to the first aspect of the present invention. FIG. 2 illustrates that the housing 4 of the device 200 comprises six separate culture dish compartments 6, each culture dish compartment being separated from the adjacent culture dish compartment 6 by a compartment walls. In FIG. 2 are shown that a culture dish 8 is accommodated in each culture dish compartments 6. The culture dish 8 rests on a shelf 34 which in FIG. 2 simple is the bottom of the culture dish compartment. At least part of the bottom of the culture dish compartments is transparent, thus allowing the image capturing device 10 and the FLIM unit 11 (or the optical parts thereof) to transmit and capture electromagnetic radiation to/from a biological material 2 accommodated in one or more wells of the culture dishes 8 from an area below the culture dish compartments 6. In FIG. 2 the transparent bottom of the culture dish compartments is in the form of transparent shelves 24.

The image capturing device 10 and the FLIM unit 11 (or parts thereof), are attached to movement means 38 for moving the image capturing device and the FLIM unit (or parts thereof), thereby allowing the image capturing device and the FLIM unit to move along the longitudinal direction X with the view to capture images of biological material being cultured in the culture wells of one or more culture dishes arranged in one or more of the culture dish compartments and also with the view to capture FLIM spectra of such biological material.

The image capturing device 10 and the FLIM unit 11 (or parts thereof) may in a general case also be configured to to move along the transversal direction Y and the direction Z, being perpendicular to the direction X and to the direction Y.

Figure 3:
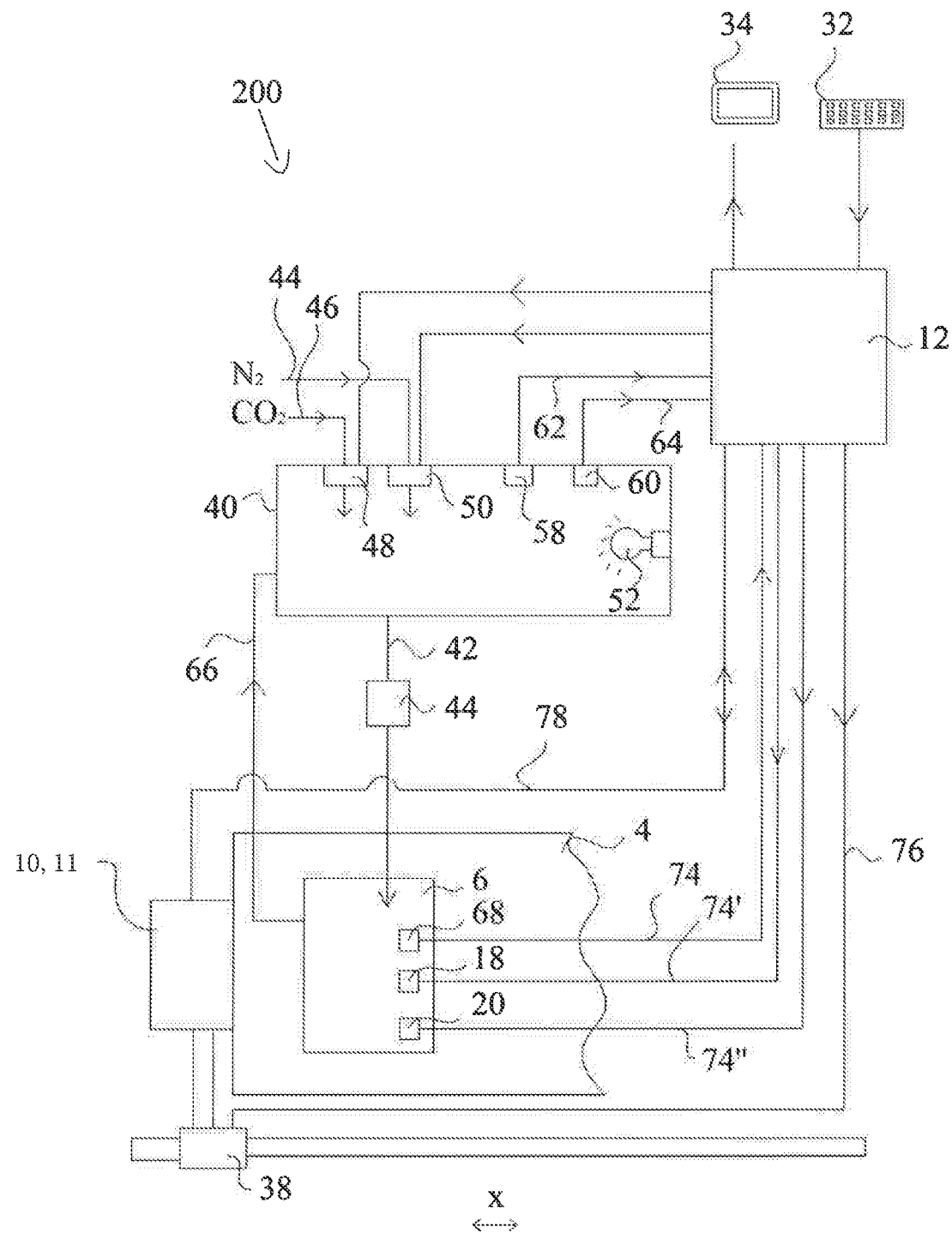
FIG. 3 schematically illustrates details of a control system for controlling a device according to the present invention.

For sake of simplicity, in FIG. 2 and also in FIG. 3 the image capturing device 10 and the FLIM unit 11 are outlined collectively as item 10,11 arranged on a common set of movement means 38.

However, the image capturing device 10 and the FLIM unit 11 may just as well each be provided with its own individual set of movement means 38.

It is seen in FIG. 2 that each culture dish compartment is having its own dedicated lid 14 which allows for introducing, removing and inspecting a culture dish accommodated in a specific compartment without imposing any adverse effects, such as altering the composition of atmosphere or altering the temperature of the atmosphere of any of the other culture dish compartments 6. Moreover, in this way no risk of contamination of the content of the culture dishes 8 in any other compartment than the specific one subject to inspection will be present.

In most cases it will be advantageous to provide the device 200 with means for providing a desired gas atmosphere in each culture dish compartments. It will furthermore in most cases be desirably to provide the device 200 with heating means and temperature sensors for regulating the temperature in each culture dish compartments.

Preferably the device 200 will also be provided with control means for controlling such parameters. This is further elaborated below.

FIG. 3 illustrates schematically details of such a control system for the device 200 according to the first aspect of the present invention. FIG. 3 shows the device 200 comprising the housing 4. The housing comprises two or more separate culture dish compartments (only one culture dish compartment is shown in FIG. 3 for the sake of simplicity). The culture dish compartment is provided with gas. The gas is flowing from a gas mixing box 40 in a conduit 42 through a filter means 44 for gas and into the interior of the culture dish compartment 6.

In FIG. 3 various parts of the control system and the gas mixing box are indicated to be located outside the housing of the device. This design may be possible. However, it may also be desirable to arrange such part inside the housing of the device. The gas mixing box comprises inlets 44,46 for gas. The gases to be supplied may preferably be $CO_2$ and $N_2$ as shown in FIG. 3. The magnitude of the flow of the gasses supplied to the gas mixing box may be regulated by the valves 48,50. Means 52 for emitting electromagnetic radiation in the UV wavelength range may be provided for gas sanitizing purposes.

The device may be provided with a control unit 12 for controlling various parameters of the operation of the device. Such a control unit is shown in FIG. 3. The control unit 12 is coupled to input means 32, such as an alphanumerical keyboard or a pointing device allowing a user to input data relating to a desired mode of operation. Furthermore, the control unit may be coupled to display means 34 allowing a user to monitor various settings of the operation of the device.

In FIG. 3 are also shown a $CO_2$ sensor 58 and an $O_2$ sensor 60. The sensors may be coupled to the control unit 12 via wires 62, 64 and the control unit may be coupled to the valves 48,50 for regulating inlet of gas. In this way it will be possible to maintain a fairly constant atmosphere of a desired gas mixture in each separate culture dish compartment 4.

Each culture dish compartment may be connected to its own dedicated gas mixing box; or alternatively, two or more culture dish compartments may share the same gas mixing box.

Normally it will not be desired to provide oxygen content in the interior of the culture dish compartments above the normal oxygen level in atmospheric air. For this reason the oxygen level may be regulated by supplying varying amounts of $CO_2$ and $N_2$. The $CO_2$ level may in turn be regulated by "dilution" with $N_2$. From the interior of the culture dish compartment is provided a conduit 66 for recirculating gas from the interior of the compartment back to the gas mixing box.

The culture dish compartment may be equipped with a temperature sensor 68 and heating means 18 and/or cooling means 20. The temperature sensor 68 and heating means 18 and the cooling means 20 are coupled via wires 74,74', 74" to the control unit 12 in such a way that feedback may be provided to the heating means 18 and the cooling means 20 from the control unit 12, based on readings of the temperature sensor 68.

The image capturing device 10 and the FLIM unit, or at least parts thereof, such as transmitting and receiving parts thereof is/are moveable, at least along the longitudinal direction X below the array of culture dish compartments. This movement is brought about by movement means 38, which is controlled by the control unit 12 via wire 76.

Information relating to sending and/or receiving information in relating to operation of the image capturing device 10 itself is transmitted through cable 78.

Figure 4:
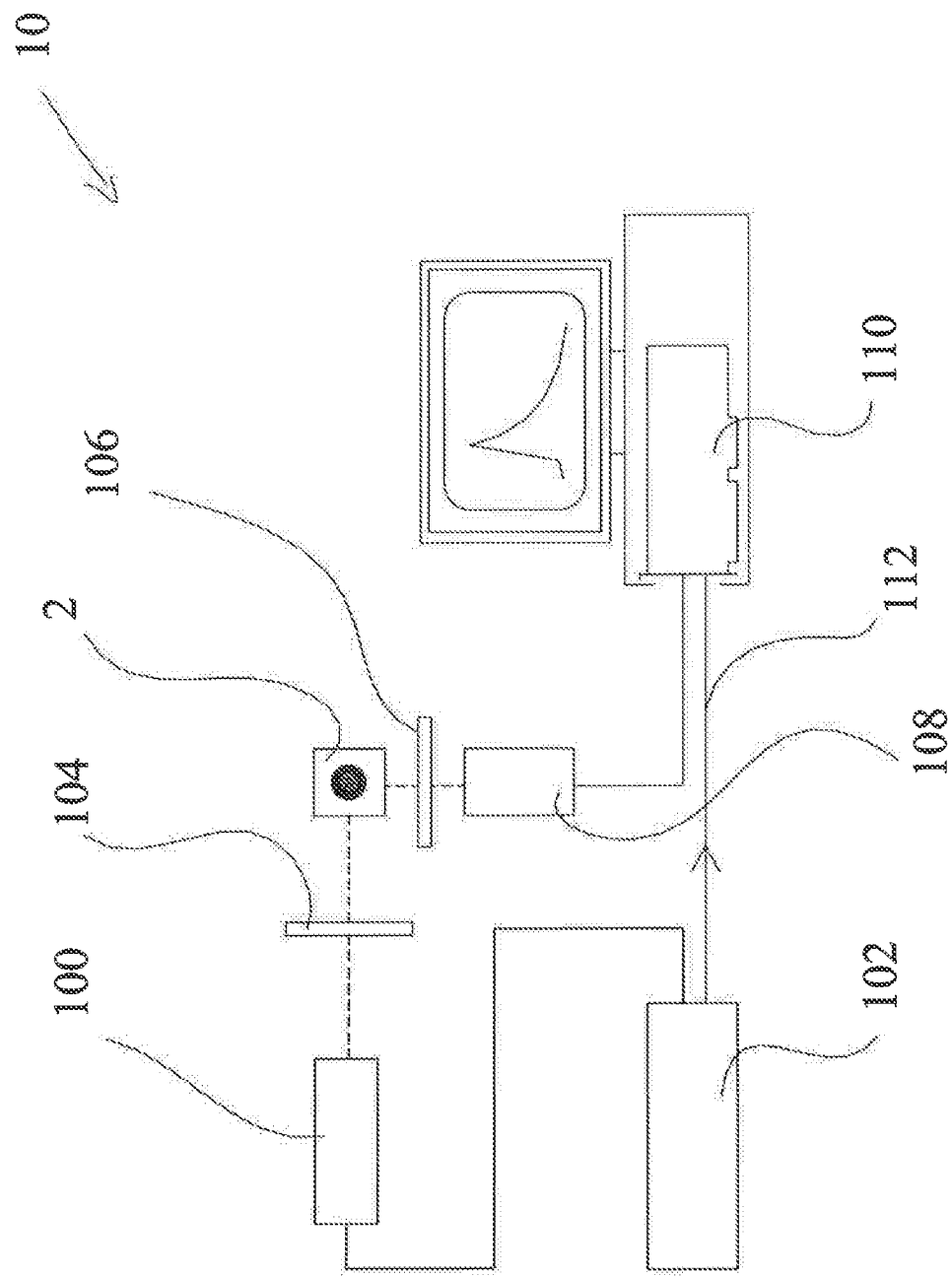
FIG. 4 illustrates a simple TCSPC set-up for fluorescence lifetime measurements.

FIG. 4 shows a simple set-up for fluorescence lifetime measurements with TCSPC. A picosecond diode laser 100 is running on its internal clock. The driver box 102 is physically separate from the actual laser head which is attached via a flexible lead. This permits to conveniently place the small laser head anywhere in the optical set-up.

The light pulses of typically 50 ps FWHM are directed at the sample of biological material 2 being accommodated in a cuvette. The light pulses are preferably being directed at the biological material using appropriate optics. A neutral density filter 104 is used to attenuate the light levels to maintain single photon statistics at the detector. Upon excitation, the fluorescent biological material or sample will emit light at a longer wavelength than that of the excitation light. The fluorescence light is filtered out against scattered excitation light by means of an optical cut-off filter 106.

Subsequently the fluorescence light is directed to the photon, via some appropriate collection optics, e.g., a microscope objective or just a lens. For timing accuracies of 200 ps FWHM, an non-costly Photomultiplier Tube 108 is sufficient. The electrical signal obtained from the detector, e.g., a small negative pulse of −20 mV, is fed to a preamplifier, and then to the TCSPC electronics 110 via a standard 50 Ohms coax cable.

Figure 5:
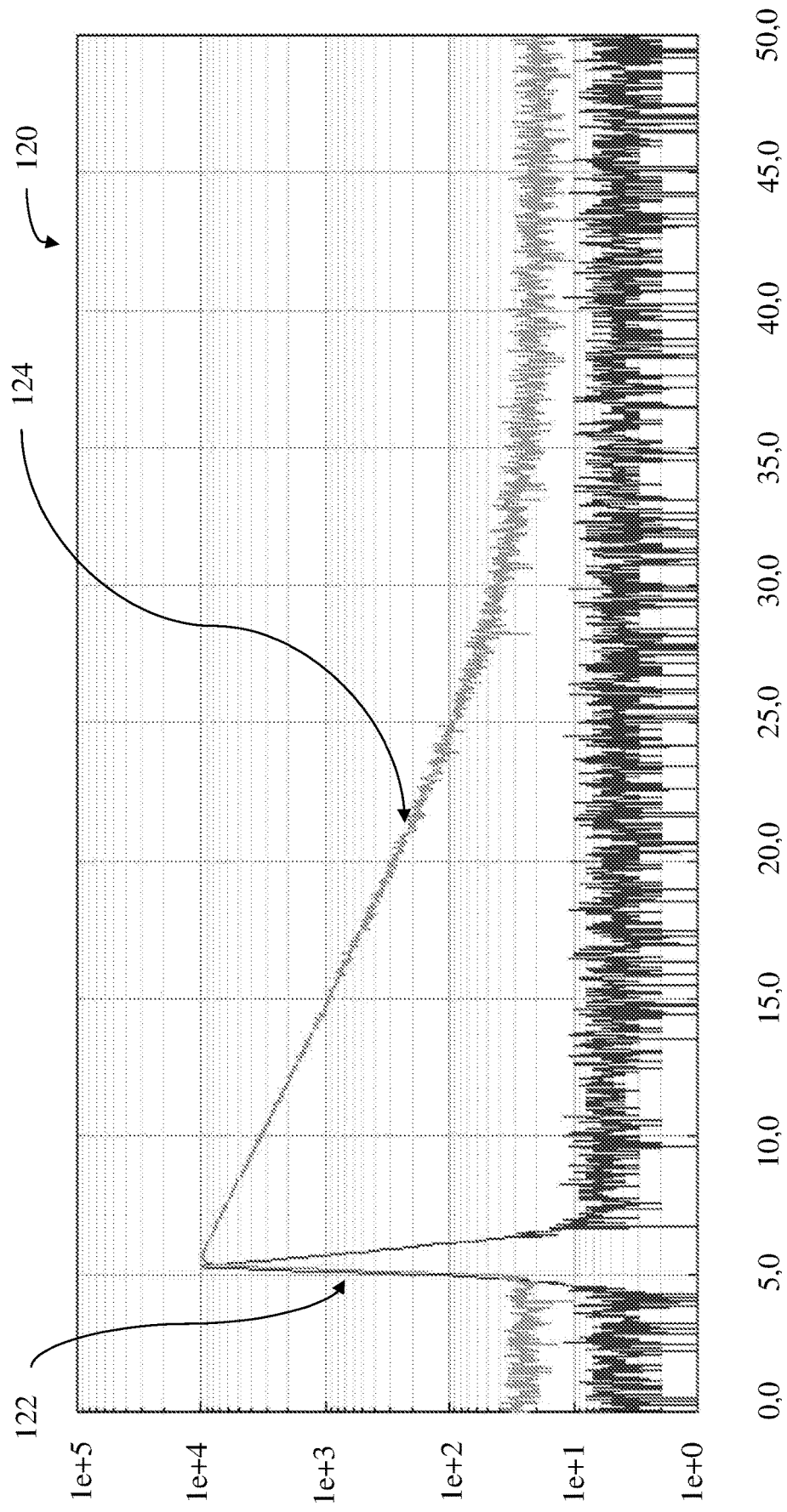
FIG. 5 illustrates a TCSPC histogram obtained with the setup of FIG. 4.

The laser driver also provides the electric sync signal 112 needed for the photon arrival time measurement. This signal (NIM standard, a narrow pulse of −800 mV) is fed to the TCSPC electronics via a standard 50 Ohms coax cable. FIG. 5 shows TCSPC histograms obtained with the setup including the TCSPC electronics illustrated in FIG. 4. Excitation source was a PDL 800-B with a 470 nm laser head running at 10 MHz repetition rate. A PDM SPAD from MPD was used for detection. The narrow, highest peak at the left hand side represents the system Instrument Response Function (IRF), here dominated by laser and detector. The other curve corresponds to the fluorescence decay from a solution of Atto 488 in water.

Atto 488 is a fluorescent dye with fairly short fluorescence lifetime (~3.8 ns). The count rate was adjusted to <1% of the laser rate to prevent pile-up. The plot in logarithmic scale shows the perfect exponential nature of the decay curve, as one would expect it.

FIG. 6 illustrates one embodiment of part of the FLIM unit to be used with the apparatus according to the present invention. FIG. 6 shows that the laser diode 100 is conveying its electromagnetic radiation via optical cables 128 and optical cable connectors 126 to the biological material 2 to be examined. Likewise, the fluorescent signal emitted from the sample is being conveyed via optical cables 128 and optical cable connector 126 to the detector 108.

As the apparatus according to the first aspect comprises an image capturing device as well as a FLIM unit, it is possible to monitor one or more viable biological material, such as oocytes or embryos and compare the metabolic state of one or more biological materials, as determined by means of a FLIM spectrum, at development stages that are comparable from one biological material to the other, as determined by means of the specific morphological appearance which is revealed by using the image capturing device.

Accordingly, in the apparatus of the first aspect of the present invention, the image capturing device is used for determining a specific morphological stage of interest of the biological material (such as the number of cell cleavages). The FLIM unit on the other hand is used for revealing metabolic stages of the biological materials.

Thereby, metabolic stages and qualities of various biological materials can be compared at morphological stages which are comparable.

Based on this, an objective assessment of the quality of an incubated biological material, compared to other biological incubated biological material, can be performed with reference to the same morphological stage of the biological material (which may vary in terms of the time frame).

Such an objective assessment is of extremely high value, not at least with the view to select viable oocytes or embryos for insertion into a female's uterus.

Although, the present invention has mainly been described with reference to human fertilization technology, it is obvious that the present invention in its various aspects likewise is applicable in many other fields of technology, including veterinary science, including fertility technology within veterinary science.

It should be understood that all features and achievements discussed above and in the appended claims in relation to one aspect of the present invention and embodiments thereof apply equally well to the other aspects of the present invention and embodiments thereof.

LIST OF REFERENCE NUMERALS

2 Biological material
4 Housing of apparatus
6 Culture dish compartment
8 Culture dish
10 Image capturing device
11 FLIM unit or parts thereof
12 Control unit
14 Lid of culture dish compartment
16 Temperature regulating means
18 Heating means
20 Cooling means
22 Gas composition regulating means
24 Transparent shelf
26 pH sensor
28 Oxygen sensor
30 Carbon dioxide sensor
32 Input means
34 Display means
36 Image processing unit
38 Movement means
40 Gas mixing box
42 Conduit
44 Inlet for gas
46 Inlet for gas
48 Valve
50 Valve
52 UV radiation means
58 $CO_2$ sensor
60 $O_2$ sensor
62 Wire
64 Wire
66 Conduit
68 Temperature sensor
74,74',74" Wires
76 Wire
78 Cable
100 Laser diode
102 Driver box
104 Neutral density filter
106 Cut-off filter
108 Detector
110 TCSPC electronics
112 Cable for conveying sync signal
120 Histogram
122 Peak of histogram
124 Decay curve
126 Optical fiber connector
128 Optical cable
200 Apparatus
300 System
X Longitudinal direction
Y Transverse direction
Z Direction perpendicular to a longitudinal and transversal direction

The invention claimed is:

1. An apparatus (200) comprising:
(a) a housing (4) having an extension in a longitudinal direction X, in a transversal direction Y, and in a direction Z perpendicular to the longitudinal direction and the transversal direction;
said housing comprising two or more culture dish compartments (6) each being adapted to accommodate one or more culture dishes (8) comprising a biological material (2);
(b) an image capturing device (10); wherein at least part of said image capturing device is configured to be movable in relation to the two or more culture dish compartments (6), thereby allowing capture of images of one or more of said biological materials (2) accommodated in said one or more culture dishes (8);
(c) a control unit (12) for controlling the operation thereof; and
(d) a FLIM unit (fluorescent lifetime imaging microscope) (11);
wherein at least part of said FLIM unit (11) is being configured to be movable in relation to the two or more culture dish compartments (6), thereby allowing capture of FLIM spectra of one or more of said biological materials (2) accommodated in said one or more culture dishes (8);

wherein said apparatus further comprises an image processing unit (36) for processing images captured by said image capturing device (10) and a spectral data processing unit for processing information relating to electromagnetic radiation captured by said FLIM unit (11);

wherein said control unit is configured to allow a user to input one or more predetermined operation protocols to be followed by said apparatus; and wherein said control unit is configured to fully automatically control said apparatus according to said one or more protocols;

wherein said apparatus is configured to determine an assessment of the quality of said viable biological material (2) during incubation on the basis of the morphological state of the biological material, as monitored by said image capturing device, in combination with the metabolic state of said biological material, as monitored by said FLIM unit.

2. An apparatus (200) according to claim 1, wherein one or more of said individual culture dish compartments (6) comprises its own individual lid (14), wherein each said lid is configured to be able to shift between an open configuration providing access to the corresponding culture dish compartment (6) and a closed configuration in which the corresponding culture dish compartment is being sealed off from the surroundings.

3. An apparatus (200) according to claim 1 furthermore comprising temperature regulating means (16) for individual and independent regulation of the temperature in one or more of said individual culture dish compartments (6).

4. An apparatus (200) according to claim 1 furthermore comprising gas composition regulating means (22) for individually regulating the gas composition in one or more of said individual culture dish compartments (6), and furthermore comprising one or more conduits (42) for conducting a gas from a gas mixing box (40) to one or more of said separate culture dish compartments (6).

5. An apparatus (200) according to claim 1 wherein in respect of one or more of said individual culture dish compartments (6), said individual culture dish compartment comprises a transparent shelf (24) for carrying a culture dish; and wherein said FLIM unit, or at least a light transmitting and a light receiving part of it, is/are arranged below said shelves and being adapted to be movable so as to enable capturing electromagnetic radiation, through said shelves (24), from said biological material (2) accommodated in any of said culture dish (8) being accommodated in any of said culture dish compartments (6).

6. An apparatus (200) according to claim 1, wherein said FLIM unit independently comprises one or more of the following elements:
a laser source in the form of a pulsed laser source;
a dichroic mirror (for separation of fluorescence signal from the excitation light);
an objective (for focusing excitation light into sample and/or for collecting fluorescence signal);
a control system for controlling said FLIM unit.

7. The apparatus according to claim 6, wherein the pulsed laser source is selected from a diode laser or a multiphoton excitation laser.

8. An apparatus (200) according to claim 1, wherein said FLIM unit is configured for auto-fluorescence of nicotine amide adenine (NADH) and/or for auto-fluorescence of flavine adenine dinucleotide (FAD) being involved in the metabolism of the biological material.

9. An apparatus (200) according to claim 1, wherein said apparatus is configured for operating in a time-correlated single photon counting (TCSPC) mode.

10. An apparatus (200) according to claim 1, wherein said apparatus is configured for operating in a FRET mode or in a FRAP mode or in a PLIM mode (Phosphorescence Lifetime Imaging Microscopy).

11. An apparatus (200) according to claim 1, wherein said apparatus during the fluorescence operations is being configured to operate in the time domain or in the frequency domain.

12. An apparatus (200) according to claim 1, wherein said apparatus is being configured to incubate two or more biological material in the form of oocytes or embryos; wherein said apparatus in respect of each specific of said two or more biological materials is being configured, based on images captured by said image capturing device (10), to identify a predetermined morphological state of said specific biological material; and wherein said apparatus is being configured, in the event that a predetermined morphological state has been reached in respect of a specific biological material, to capture a FLIM spectrum of said specific biological material.

13. An apparatus (200) according to claim 12, wherein said apparatus is being configured, in respect of each specific of said two or more biological materials, to identify two or more different and predetermined morphological states, based on said images captured by said image capturing device (10), of that specific biological material, and wherein in the event of each such different and predetermined morphological state has been reached in respect of a specific biological material, said apparatus is being configured to capture a FLIM spectrum of said specific biological material in respect of each such predetermined morphological state.

14. An apparatus (200) according to claim 13, wherein said apparatus in respect of each of said two or more biological materials is being configured for analyzing differences of the FLIM spectra corresponding to two or more different morphological states of the same biological material.

15. A method for incubation of a viable biological material (2), said method comprising providing the apparatus (200) according to claim 1, accommodating one or more culture dishes each comprising biological material in separate culture dish compartments of said apparatus, and incubating said biological materials at incubation conditions.

16. The method according to claim 15 for empirically determining optimum protocols relating to physical and/or chemical conditions of a biological material (2) during the incubation thereof.

17. A method for assessing optimum incubation conditions for a viable biological material, said method comprising the following steps:
i) providing an apparatus (200) according to claim 1;
ii) accommodating at least two culture dishes, each comprising one or more viable biological materials in separate culture dish compartments of said apparatus;
iii) incubating said biological materials at incubation conditions, wherein the physical and/or chemical incubation conditions in respect of biological material being accommodated in one culture dish compartment differs by one or more parameters from the physical and/or chemical incubation conditions in respect of biological material being accommodated in another culture dish compartment;

iv) during step iii), using the FLIM unit of said apparatus for capturing FLIM images;

v) assessment of the quality of the biological material based on said FLIM images.

18. A method according to claim 17, wherein the most optimum physical and/or chemical incubation conditions is being determined, based on said FLIM images.

19. A system (300) for incubation of a viable biological material; said system comprises:
    an apparatus (200) according to claim 1, in combination with
    one or more culture dishes (8).

20. A method for incubation of a viable biological material (2), said method comprising providing the system (300) according to claim 19, accommodating one or more culture dishes each comprising biological material in separate culture dish compartments of said system, and incubating said biological materials at incubation conditions.

21. The method according to claim 20 for empirically determining optimum protocols relating to physical and/or chemical conditions of a biological material (2) during the incubation thereof.

22. A method for assessing optimum incubation conditions for a viable biological material, said method comprising the following steps:
    i) providing a system (300) according to claim 19;
    ii) accommodating at least two culture dishes, each comprising one or more viable biological materials in separate culture dish compartments of said system;
    iii) incubating said biological materials at incubation conditions, wherein the physical and/or chemical incubation conditions in respect of biological material being accommodated in one culture dish compartment differs by one or more parameters from the physical and/or chemical incubation conditions in respect of biological material being accommodated in another culture dish compartment;
    iv) during step iii), using the FLIM unit of said apparatus for capturing FLIM images;
    v) assessment of the quality of the biological material based on said FLIM images.

23. The method according to claim 22, wherein the most optimum physical and/or chemical incubation conditions is being determined, based on said FLIM images.

* * * * *